US011583627B1

(12) United States Patent
Forouzandeh et al.

(10) Patent No.: US 11,583,627 B1
(45) Date of Patent: Feb. 21, 2023

(54) IMPLANTABLE DRUG STORAGE DEVICES FOR DRUG DELIVERY

(71) Applicant: UNIVERSITY OF SOUTH FLORIDA, Tampa, FL (US)

(72) Inventors: Farzad Forouzandeh, Rochester, NY (US); David Borkholder, Canandaigua, NY (US); Robert Frisina, Tampa, FL (US); Joseph Walton, Tampa, FL (US); Xiaoxia Zhu, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 554 days.

(21) Appl. No.: 16/657,981

(22) Filed: Oct. 18, 2019

Related U.S. Application Data (60) Provisional application No. 62/747,413, filed on Oct. 18, 2018.

(51) Int. Cl.
| | |
|---|---|
| *A61M 5/142* | (2006.01) |
| *A61M 5/145* | (2006.01) |
| *A61M 5/20* | (2006.01) |
| *A61M 39/06* | (2006.01) |
| A61M 39/00 | (2006.01) |
| A61M 39/02 | (2006.01) |

(52) U.S. Cl.
CPC ........ *A61M 5/14276* (2013.01); *A61M 5/145* (2013.01); *A61M 5/14224* (2013.01); *A61M 5/14593* (2013.01); *A61M 5/204* (2013.01); *A61M 39/06* (2013.01); *A61M 2039/0072* (2013.01); *A61M 2039/0081* (2013.01); *A61M 2039/027* (2013.01); *A61M 2205/0244* (2013.01)

(58) Field of Classification Search
CPC .......... A61M 39/0208; A61M 5/14276; A61M 5/145; A61M 2205/0244; F04B 43/043; F04B 19/006
See application file for complete search history.

(56) References Cited

U.S. PATENT DOCUMENTS

| 4,084,718 A | 4/1978 | Wadsworth |
| 4,655,765 A | 4/1987 | Swift |

(Continued)

OTHER PUBLICATIONS

Guo-Hua Feng and Eun Sok Kim, "Piezoelectrically actuated dome-shaped diaphragm micropump," in Journal of Microelectromechanical Systems, vol. 14, No. 2, pp. 192-199, Apr. 2005, doi: 10.1109/JMEMS.2004.839331. (Year: 2005).*

(Continued)

*Primary Examiner* — Jenna Zhang
(74) *Attorney, Agent, or Firm* — Quarles and Brady LLP (57) ABSTRACT

In one embodiment, a fluid storage device includes a rigid outer housing that defines a septum cavity, a reservoir cavity, and a channel that extends between the two cavities, the outer housing further defining an outlet in fluid communication with the reservoir cavity, a septum provided within the septum cavity, the septum being made of an elastic polymer and facilitating refilling of the fluid storage device, and a thin, collapsible membrane that does not generate significant restoring forces when it is deformed as fluid is drawn from the reservoir cavity and, therefore, does not completely or partially return to its initial non-deformed shape even if the outlet of the device remains open after doses are administered.

20 Claims, 5 Drawing Sheets

(56) References Cited

U.S. PATENT DOCUMENTS

| | | | |
|---|---|---|---|
| 6,730,606 B1 | 5/2004 | Steinbach | |
| 6,764,472 B1 | 7/2004 | Burke | |
| 7,883,717 B2 | 2/2011 | Varner | |
| 9,561,352 B2 | 2/2017 | Martin | |
| 10,307,581 B2 | 6/2019 | Hibdon | |
| 2007/0255260 A1 | 11/2007 | Haase | |
| 2007/0282308 A1 | 12/2007 | Bell | |
| 2009/0306594 A1* | 12/2009 | Pang | A61M 5/14276 307/66 |
| 2009/0306595 A1* | 12/2009 | Shih | A61M 5/36 141/2 |
| 2010/0069891 A1 | 3/2010 | Ginggen | |
| 2011/0054390 A1 | 3/2011 | Searle | |
| 2011/0309552 A1* | 12/2011 | Amirouche | A61M 5/16804 264/331.11 |
| 2014/0172090 A1* | 6/2014 | Gunn | A61F 9/00781 623/6.22 |
| 2015/0032051 A1 | 1/2015 | Brandt | |
| 2015/0032084 A1 | 1/2015 | Cabiri | |
| 2015/0190568 A1* | 7/2015 | Shih | A61M 5/14276 604/891.1 |
| 2017/0043151 A1 | 2/2017 | Bellrichard | |
| 2019/0070399 A1 | 3/2019 | Casiello | |
| 2019/0199560 A1 | 6/2019 | Bossard et al. | |
| 2019/0269850 A1* | 9/2019 | Shih | A61M 5/172 |

OTHER PUBLICATIONS

Li PY, Sheybani R, Gutierrez CA, Kuo JT, Meng E. A Parylene Bellows Electrochemical Actuator. J Microelectromech Syst. Jan. 1, 2010;19(1):215-228. doi: 10.1109/jmems.2009.2032670. PMID: 21318081; PMCID: PMC3035913. (Year: 2010).*

Gensler (Rapid fabrication and characterization of MEMS Parylene C bellows for large deflection applications; J. Micromech. Microeng. 22 11(2012) 115031) (Year: 2012).*

Gensler, et al. "Rapid fabrication and characterization of MEMS Parylene C bellows for large deflection applications", Journal of Micromechanics and Microengineering 22.11 (2012): 115031.

Lo, et al., "A refillable micro-fabricated drug delivery device for treatment of ocular diseases", Lab on a Chip, vol. 8, No. 7, p. 1027, 2008.

Song, et al. "A self-powered implantable drug-delivery system using biokinetic energy", Advanced Materials, vol. 29, No. 11, p. 1605668, 2017.

Morimoto, et al. "Balloon Pump with Floating Valves for Portable Liquid Delivery", Micromachines MDPI, 2016.

* cited by examiner

IMPLANTABLE DRUG STORAGE DEVICES FOR DRUG DELIVERY

CROSS-REFERENCE TO RELATED APPLICATION

This application claims priority to U.S. Provisional Application Ser. No. 62/747,413, filed Oct. 18, 2018, which is hereby incorporated by reference herein in its entirety.

NOTICE OF GOVERNMENT-SPONSORED RESEARCH

This invention was made with Government support under grant contract number R01DC014568 awarded by the National Institutes of Health (NIH). The Government has certain rights in the invention.

BACKGROUND

Drug delivery systems have become of interest to researchers because they can improve therapeutic response by providing more consistent drug blood levels as compared to immediate release or sustained release parenteral depot. The development of microscale reservoir-based delivery systems has resulted in miniaturization of drug delivery systems while still enabling more precise control of the delivery rate for both systemic and site-directed delivery.

Implantable drug delivery systems generally fall into two categories: passive and active. Active implantable drug delivery systems generally comprise a drug reservoir that stores the drug-containing fluid (e.g., liquid) to be administered to a subject and a micropump that delivers small precise volumes of the fluid to the target organ. The dynamics between the fluid stored in the reservoir and the downstream environment when the micropump is deactivated is an important consideration in the design of the reservoirs. Such reservoirs are typically made of a flexible material that enables the reservoir to deform as fluid is drawn from the reservoir.

Unfortunately, the properties of typical reservoirs are such that the reservoirs are affected by restoring forces that tend to restore the reservoir to its initial shape. This is disadvantageous as it can create negative pressure that results in backflow of the fluid back into the reservoir. When this occurs, the subject in which the drug delivery system is implanted may not receive the full prescribed dose of medication. Even when such effects are accounted for by increasing operation of the micropump to compensate for backflow, the dose may still vary over time as the restoring force may change (e.g., increase) as the reservoir becomes further and further deformed. In addition, the negative pressure created by the restoring forces can decrease the efficiency of the micropump.

While the effects of the restoring forces acting upon a reservoir can be counteracted by using a normally closed system that comprises a valve that closes when the micropump is not operated, there are advantages of normally open systems that do not require such components, such as smaller size, lower power consumption, and less complexity. Accordingly, it can be appreciated that it would be desirable to have a reservoir for use in a normally open implantable drug delivery system that is not adversely affected by restoring forces.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a reservoir for use in a normally open implantable drug delivery system that is not adversely affected by restoring forces. Disclosed herein are examples of such drug storage devices that include a reservoir that is at least partially formed by a thin, flexible membrane that does not generate significant restoring forces when it is deformed as fluid is drawn from the reservoir for administration to a subject (e.g., patient) and, therefore, does not completely or partially return to its initial non-deformed shape, even if the outlet of the device remains open after doses are administered, as is the case with "normally open" devices or systems that comprise no valves or other actuatable devices that are configured to impede the flow of fluid to and from the reservoir. In some embodiments, the flexible membrane comprises a thin layer of parylene. In further embodiments, the drug storage device also comprises a separate septum used for refilling of the device that is compressed within the device so as to improve its self-healing capabilities.

In the following disclosure, various specific embodiments are described. It is to be understood that those embodiments are example implementations of the disclosed inventions and that alternative embodiments are possible. Such alternative embodiments include hybrid embodiments that include features from different disclosed embodiments. All such embodiments are intended to fall within the scope of this disclosure.

Disclosed herein are normally open implantable drug storage devices that can be integrated with a micropump to form an active, normally open, implantable drug delivery system. The drug storage devices have a small footprint and a planar form factor and are, therefore, well suited for subcutaneous implantation, whether it be in an animal or a human being. In some embodiments, three-dimensional printing technology can be used to fabricate the implantable drug storage device. The drug storage devices each comprise a reservoir that includes a thin, flexible membrane that minimizes restoring forces as fluid is drawn from the reservoir. The drug storage device further includes a separate self-healing septum whose thickness is minimized using compression that can be punctured thousands of times for purposes of device refilling without leaking. Example embodiments of the drug storage device are described below as are experiments that were performed using prototype devices to evaluate the effectiveness of the drug storage device designs.

Figure 1:
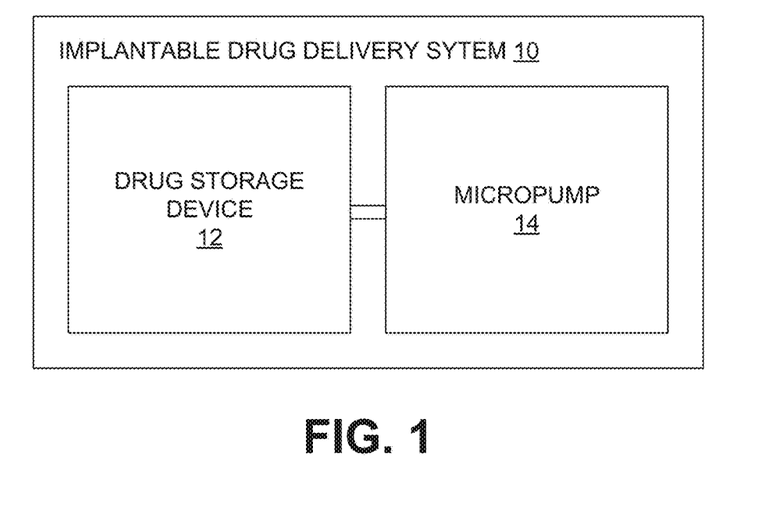
FIG. 1 is a schematic diagram illustrating an example implantable drug delivery system.

FIG. 1 schematically illustrates an implantable drug delivery system 10 that comprises a drug storage device 12 and a separate micropump 14. The drug storage device 12 is configured to store a fluid (e.g., liquid) that contains a drug that is to be administered to a subject in which the drug delivery system 10 is implanted through operation of the micropump 14. As storage device 12 is in a general sense configured to store a fluid, the storage device 12 can be referred to as a fluid storage device. For the remainder of this disclosure, however, the disclosed storage devices will be referred to as a drug storage devices. While the drug storage device 12 is shown and described herein as an independent component, it is noted that, in other embodiments, the drug storage device and the micropump can be combined together to form a single integrated drug delivery device. Accordingly, while embodiments of independent drug storage devices are described below, it is noted that the devices need not be independent of a micropump used to deliver the fluid that the drug storage device contains.

Figure 2:
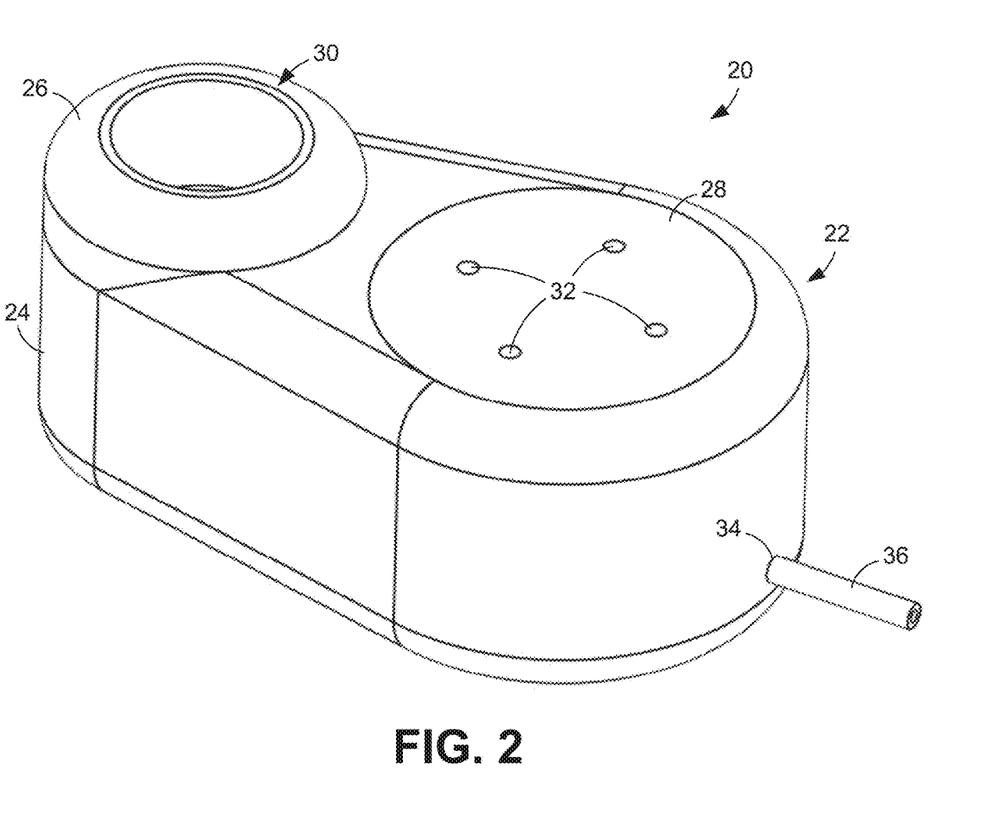
FIG. 2 is a perspective view of an embodiment of a normally open drug storage device that can comprise part of the system of FIG. 1.

FIG. 2 illustrates an example embodiment for a drug storage device 20, which can be used with a separate or integrated micropump (not shown). It is assumed that the drug storage device, as well as the drug delivery system in which it is used, is a "normally open" device/system that comprises no valves or other actuatable devices that are configured to impede the flow of fluid to and from the device.

As depicted in FIG. 2, the drug storage device 20 generally comprises a rigid outer housing 22 that provides structural integrity to the device and contains various internal components of the device, which are described below. In some embodiments, the outer housing 22 is made of a polymeric material such as dental resins, nylon, or polytetrafluoroethylene (PTFE) or a metal material such as stainless steel, titanium, or aluminum, and optionally can be coated with a biocompatible polymer, such as poly(p-xylylene), also known as parylene, a USP Class VI material. Notably, parylene minimizes the risk of inflammation from direct contact to body tissues and has less permeability to fluid as compared to other materials used for implant construction. In some embodiments, the housing 22, as well as other components of the drug storage device 20 can be formed using an additive manufacturing fabrication process, such as three-dimensional-printing (e.g., stereolithography (SLA)).

The outer housing 22 can be composed of separately components that are assembled together in order to form the complete housing. In the illustrated embodiment, the outer housing 22 comprises a base member 24 to which are connected a septum cavity cap 26 and a reservoir cavity cap 28. In some embodiments, each of these components can be separately fabricated and coated with a layer of biocompatible polymer, such as parylene. In fact, each component of the drug storage device 20 that may come into contact with the tissues or fluids of the subject can either be coated with this material or made of this material. As shown in FIG. 2, the septum cavity cap 26 is provided on the top side of the outer housing 22 at a first end of the device 20, while the reservoir cavity cap 28 is also provided on the top side of the housing at a second end of the device. As described in greater detail below in relation to the cross-sectional view of FIG. 3, the septum cavity cap 26 covers an internal septum cavity in which a septum is provided and the reservoir cavity cap 28 covers an internal reservoir cavity in which a reservoir is provided. As is apparent from FIG. 2, the septum cavity cap 26 includes a refill port 30 through which a needle of a syringe can be passed to refill the drug storage device 20. In addition, the septum cavity cap 26 forms a raised peripheral ridge on the top of the housing 22 that is higher the reminder of the top surface of the housing. When provided, this ridge enables subcutaneous palpation and may be visible to a medical professional or scientist to assist that person in locating the refill port 30. With further reference to FIG. 2, the reservoir cavity cap 28 includes vent openings 32 that enable fluid to pass in and out of the reservoir cavity above a membrane of the reservoir.

Also visible in FIG. 2 is an outlet 34 that is formed in the base member 24 of the outer housing 22 at the bottom of the second end of the housing. As described below, this outlet 34 is in fluid communication with the reservoir in which the fluid to be administered is contained. Extending outward from the outlet 34 is an outlet tube 36 through which the fluid contained in the reservoir can be drawn by the micropump. In some embodiments, the outlet tube 36 is configured to connect to an inlet of the micropump.

Figure 3:
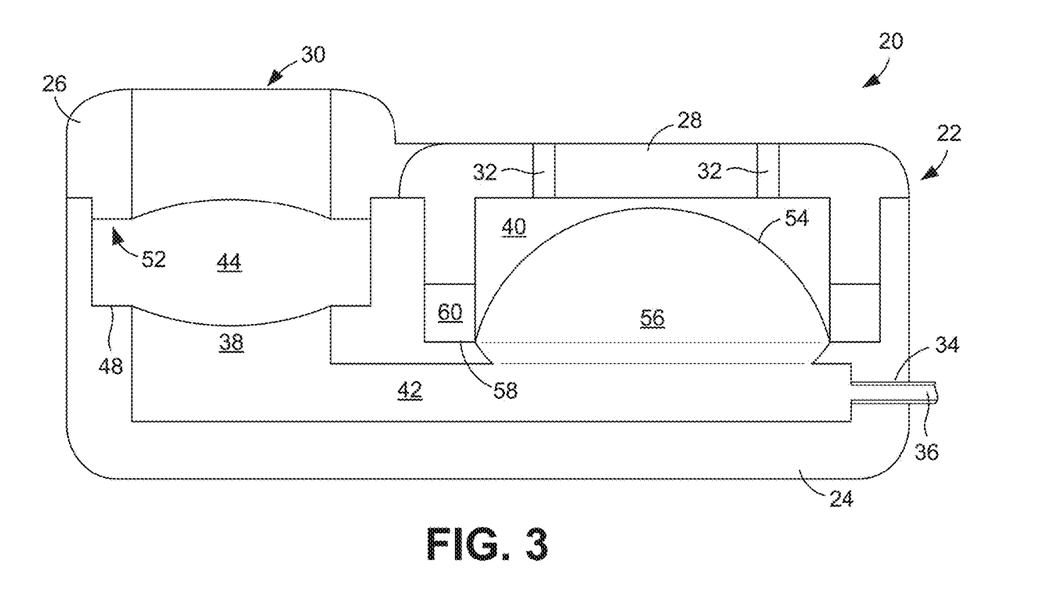
FIG. 3 is a cross-sectional side view of the drug storage device shown in FIG. 2.

Referring next to FIG. 3, the drug storage device 20 is shown in a cross-sectional side view taken along a central longitudinal axis of the device extending from the first end of the device to its second end. Visible in this figure are the septum cavity 38, the reservoir cavity 40, and a channel 42 that extends between the two cavities. Disposed in the septum cavity 38 is a self-healing flexible septum 44 that is configured to enable repeated refilling of the drug storage device 20. In some embodiments, the septum 44 comprises a generally cylindrical element that is made of an elastic polymeric material, such as biocompatible silicone. Like the components of the housing 22, the septum 44 can be coated with a layer of parylene.

Figure 4A:
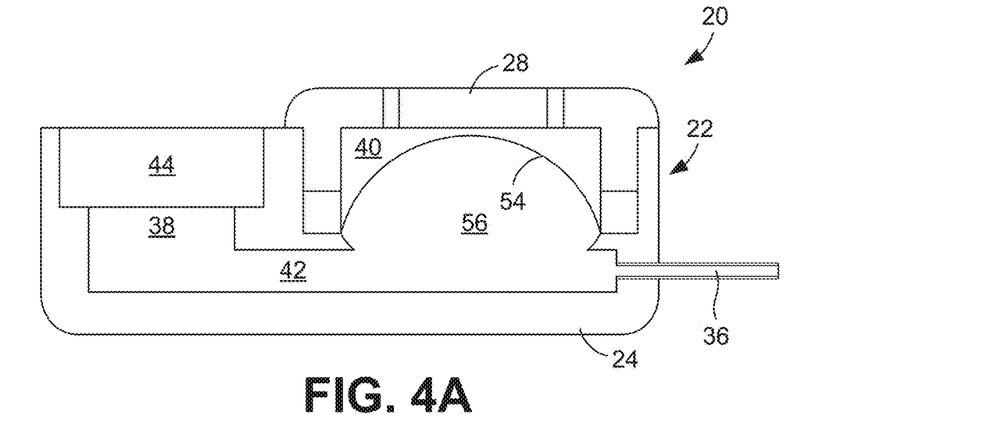
FIGS. 4A-4C are cross-sectional side views of the drug storage device shown in FIG. 2, illustrating compression of a septum of the device and deformation of a reservoir membrane of the device.

As is apparent from FIG. 3, the peripheral edges of the septum 44 are supported by an arcuate ledge 48 located within the septum cavity 38 and defined by the base member 24. The peripheral edges of the septum 44 are compressed against the ledge 48 by an annular compression ring 52 formed on the bottom of the septum cavity cap 26. The compressive forces applied to the septum 44 by the compression ring 52 serves multiple purposes. First, it forms a tight seal around the edges of the septum 44 that prevents leakage of the fluid contained within the drug storage device 20. Second, it stabilizes the septum 44 within the septum cavity 38 to ensure the septum is not displaced during refilling. Third, it compresses the septum radially inward toward its center to ensure that the holes formed by refilling needles are immediately closed after each refilling event. This radial, inward compression causes the center of the septum to bow outward. This phenomenon is apparent from FIGS. 4A and 4B. FIG. 4A shows the drug storage device 20 before the septum cavity cap 26 is connected to the base member 24 of the outer housing 22, and before the drug storage device is filled. As is apparent from this figure, the septum 44 is initially rectangular as viewed from the side.

Figure 4B:
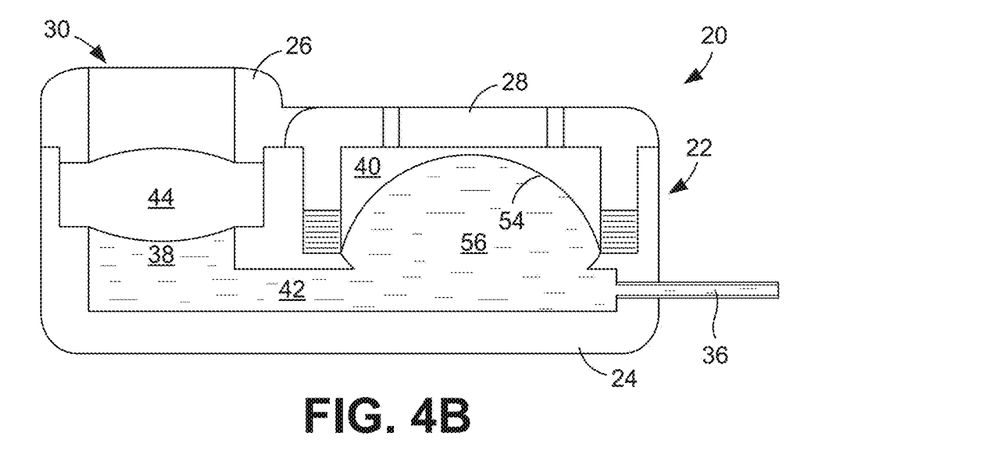

In FIG. 4B, the septum cavity cap 26 has been seated on the base member 24 and the drug storage device 20 has been filled with fluid (depicted by short horizontal lines). When the septum cavity cap 26 is seated in this manner, the peripheral edges of the septum 44 are compressed, thereby reducing its thickness of the septum around its periphery and increasing the thickness at its center, resulting in curved upper and lower central surfaces. During refilling of the drug storage device 20, a needle of a syringe can be passed through the skin of the subject, through the refill port 30, and through the septum 44 to refill the portion of the septum cavity 38 located below the septum. The presence of the base member 24 below the septum 44 (in the orientation of the figures) limits the depth to which the needle can be inserted. Once refilling is completed, the needle can be withdrawn and the hole it formed through the septum 44 is tightly closed, thereby preventing leaks.

As a fourth benefit of septum compression is that it enables a significant reduction of the septum thickness without adversely impacting its self-healing capabilities. In some embodiments, the septum 44 can be approximately 0.5 to 3 mm thick. These small dimensions further enable reduction of the overall thickness of the drug storage device 20. In some embodiments, the drug storage device 20 is no more than approximately 3 mm thick.

Referring back to FIG. 3, disposed in the internal reservoir cavity 40 is a thin, flexible, and collapsible reservoir membrane 54 that, along with the base member 24, defines a reservoir 56 in which fluid can be stored prior to administration to the subject. As shown in FIG. 3, the reservoir membrane 54 can initially have a rounded dome shape. In the example of FIG. 3, the reservoir membrane 54 is generally hemispherical. As with the peripheral edges of the septum 44, the peripheral edges of the reservoir membrane 54 are supported by an arcuate ledge 58 that is located within the internal reservoir cavity 40 and defined by the base member 24. The edges of the reservoir membrane 54 are compressed into the ledge 58 by a gasket 60 (e.g., an O-ring) that is itself is compressed into the reservoir membrane 54 by the reservoir cavity cap 28. This compression of the edges of the reservoir membrane also forms a tight seal. In some embodiments, the gasket 60 is also made of an elastic polymeric material, such as biocompatible silicone.

The reservoir membrane 54 can be made of one or more layers of flexible biocompatible polymer material. In some embodiments, the reservoir membrane 54 comprises a single layer of silicone, which has a Young's modulus of approximately 1 MPa or parylene (e.g., parylene C), which has a Young's modulus of approximately 2 to 3 GPa. The reservoir membrane 54 can have a thickness that is no greater than 100 µm and a small as approximately 2 to 20 µm. Both of these parameters (i.e., Young's modulus of the material and thickness of the membrane) impact the reservoir membrane's ability to deform without creating significant restoring forces. Accordingly, adjustment of one of the parameters may enable or require adjustment of the other parameter in order to achieve the desired membrane properties. For example, if the Young's modulus of the material used to form the reservoir membrane 54 is relatively high, the membrane can be thinner. If, on the other hand, the Young's modulus is relatively low, the membrane 54 may need to be thicker to perform as desired.

Figure 4C:
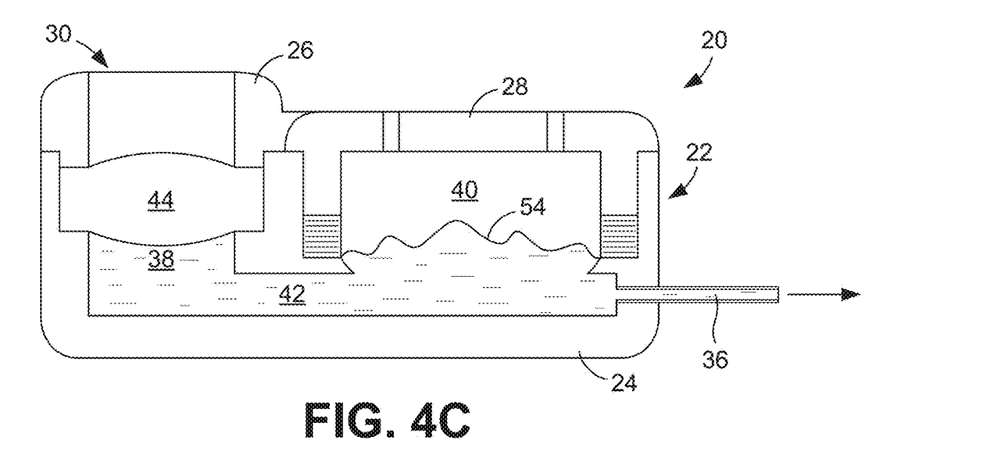

The material properties and thinness of the reservoir membrane 54 together ensure that, when the membrane readily collapses as fluid is discharged from the reservoir 56 through the outlet 34 and outlet tube 36, no significant restoring forces are generated within the membrane that cause the membrane to completely or partially return to its initial non-deformed shape, even if the outlet or tube remains open after the micropump ceases to operate, as is the case with normally open systems and devices. Avoiding such "original shape recovery" is important as it can cause undesirable backflow of fluid through the outlet/tube and back into the reservoir. As used above, the term "significant restoring forces" are restoring forces that are large enough to cause the reservoir membrane to at least begin to expand toward its non-deformed state. Notably, the thinness of the reservoir membrane 54 is achievable at least in part because the septum 44 is a separate component from the reservoir membrane. FIG. 4C illustrates deformability of the reservoir membrane 54. As shown in this figure, as fluid within the internal space defined by the reservoir membrane 54 is drawn out of the drug storage device 20 through the outlet tube 36 due to operation of the micropump, the membrane collapses toward the base member 24 without returning to its initial dome shape.

As noted above, the drug storage device 20 is a normally open device, meaning that it comprises no valves or other actuatable devices that are configured to impede the flow of fluid to or out of the outlet tube 36 when the micropump is not operating.

Drug storage devices of the type described above were fabricated for evaluation purposes. One goal was to fabricate drug storage devices having a thickness (height) of no more than 3 mm, which has been shown to be suitable for long-term subcutaneous implantation in mice. The base member of the housing was three-dimensionally printed (Form 2, Formlabs Inc., MA, USA) using a rigid biocompatible polymer material (Dental SG resin, Formlabs Inc., MA, USA). Polyurethane-based catheter microtubing (10=125 µm, 00=250 µm; Micro-Renathane® Catheter Tubing, Braintree Scientific Inc., MA, LISA) was fixed and sealed within the outlet of the base member using cyanoacrylate. The structure was then coated with a 1 µm thick layer of parylene using a parylene deposition system PDS 2010 LABCOATER™ 2 (Specialty Coating Systems, Indianapolis, Ind., USA). Housings having reservoir cavities having three different capacities, i.e., 1 µL, 10 µL, and 100 µL, were fabricated. These reservoir cavities had diameters of approximately 1.3 mm, 3.1 mm, and 10 mm, respectively.

Next, the reservoir membranes were fabricated in situ on the base member. As described below, three different thicknesses of reservoir membranes were fabricated for the three different reservoir capacities. Each reservoir membrane was optimized for 100 kPa backpressure, which is four times larger than the maximum physiological backpressure in human beings. To form the reservoir membrane, molten polyethylene glycol (PEG) was deposited within the reservoir cavity to form a sacrificial support structure having the dome shape desired for the reservoir membrane due to surface tension. In other embodiments, however, such as those in which the dome is significantly larger, the sacrificial support structure can be separately molded and then transferred to the reservoir cavity.

PEG (1,500 Mn, melting point: 37° C., Sigma-Aldrich, MO, USA) was chosen for the sacrificial structure due to its biocompatibility and solubility in water. PEG was melted at 70° C. on a hotplate and mixed with a food dye (McCormick Food Color and Egg Dye, McCormick & CO., MD, USA) for visual confirmation of its release. Using a heated micropipette (70° C.), PEG was deposited on the coated base member as it was held at room temperature. The coated base member was treated with hydrophobic spray (Scotchgard™ Fabric & Upholstery Protector, 3M Co, MN, USA) prior to deposition of the PEG to facilitate quick solidification of the PEG and prevent the PEG from flowing past the gasket 60 and into the channel that extends between the septum cavity and the reservoir cavity and the space that.

In some embodiments, improved reservoir membrane performance can be achieved by ensuring that the sacrificial support structure is very smooth. For example, when PEG1500 was used to form a first sacrificial support structure, the surface of the structure had an estimated roughness of approximately 200 µm. When PEG1000 was used to form a second sacrificial support structure, however, the surface of the structure had an estimated roughness of approximately 50 µm. It was later observed that the reservoir membrane formed on the second structure exhibited improved performance.

Next, a layer of parylene was deposited on the solidified sacrificial support structure to form the reservoir membrane. The preferred thicknesses of the parylene layers were estimated for each reservoir cavity size based on thin-walled spherical pressure for each reservoir capacity:

$$\sigma = pr/2t \tag{1}$$

where σ, p, r, and t represent tensile stress on the membrane, internal pressure, cavity radius, and membrane thickness, respectively. The reservoir membrane is designed for 100 kPa backpressure (p=100 kPa), while the radius was determined based on overall thickness and capacity of the device. The thicknesses of the reservoir membrane for each cavity size was calculated to achieve membrane stresses smaller than the tensile strength of parylene (69 MPa) by a factor of 5. These reservoir membrane thicknesses were 2.7 µm, 5.6 µm, and 18.1 µm for the 1 µL, 10 µL, and 100 µL capacities, respectively.

Silicone rubber (MED-6215, NuSil™ Technology LLC, CA, USA) gaskets with 0.5 mm width and height dimensions and inner diameters of 1.3 mm, 3.1 mm, and 10 mm were micro-molded using a parylene-coated aluminum mold fabricated with conventional machining. The gaskets were cured, placed within the reservoir cavities, and compressed using a parylene-coated reservoir cavity cap. Notably, the reservoir cavity cap also protects the reservoir membrane from external mechanical stresses. The vent openings in the reservoir cavity cap were 0.2 mm in diameter to enable ingress and egress of fluid from the space between the cap and the reservoir membrane during filling and discharging. These holes are smaller than the smallest refilling needle size for the drug storage device (30 Ga, 311 um OD) to avoid inadvertent puncture of the membrane during subcutaneous refilling.

Under visual observation using a microscope (Motic SMZ-168), the base member was heated on a hotplate at 70° C. to melt the PEG, enabling it to be rinsed away with 100 mL 70° C. deionized (DI) water and leaving a dome-shaped reservoir membrane. Silicone septa with 2.5 mm diameters and 1 mm thicknesses were micro-molded using parylene-coated three-dimensionally printed molds. The septa were cured and then coated with a 1 µm thick parylene layer. The septa were placed in the septum cavities, and then the septum cavity caps were affixed to the base member using cyanoacrylate. The bottom edges of each septum cavity cap formed a 0.2 mm thick compression ring (1.8 mm ID, 2.5 mm OD) that compressed the edges of the septa to provide internal stresses for improving its self-healing properties. A raised peripheral ridge (1.8 mm ID, 3 mm OD, 0.5 mm thickness) was integrated on top of the septum cavity cap to facilitate palpation for subcutaneous refilling. All the surfaces were filleted to minimize potential mechanical inflammation after implantation.

A 10 µL drug storage device was integrated with an implantable micropump for inner ear drug delivery to demonstrate the integrability of the drug storage device with a micropump. A miniature container was three-dimensionally printed for the micropump and its overall thickness was limited to 3 mm. Fillets with 1 mm radius were applied to the container walls to provide curved surfaces to improve long-term subcutaneous implantability. The micropump was placed in the container and the outlet tube was sealed to the drug storage device outlet using cyanoacrylate. The micropump was then fixed in the container using cyanoacrylate and silicone rubber (MED-6215, NuSil™ Technology LLC, CA, USA) was poured in the container and cured at room temperature for 48 hrs. The entire microsystem except the reservoir cavity cap was covered with a thin layer of silicone and then cured.

The septum and the reservoir membrane were decoupled and separately tested to assess their functionalities. Two separate sets of test rigs were designed and fabricated for this purpose.

The septum was tested utilizing separately fabricated septum samples. A pneumatic puncture device was designed and fabricated to hold the septum sample and automatically puncture the septum in a single location to test the worst-case scenario. A miniature cylinder (SM-3-1, Clippard Co., OH, USA) of the puncture device was positioned above the sample and an electronic pressure regulator (ITV2030-31N2BL4, SMC Co., Tokyo, Japan) was connected to the cylinder and fed with sine waves having a frequency of 0.2 Hz set by a signal generator to simulate a realistic manual puncture speed. A needle was affixed to a three-dimensionally printed needle holder, which was press-fit to the piston of the cylinder.

Commercially available 27 Ga and 30 Ga (413 µm and 311 µm OD) needles were used for the puncture tests. These sizes were selected as a trade-off between maximizing needle and septum lifetime: the needles need to be large enough to puncture through the skin and the septum without bending the tip, while still being small enough to minimize septum damage. Furthermore, the diameter of the refilling port of the septum cavity cap is 1.8 mm, making needle sizes larger than 27 Ga impractical. The needles were machined to a non-coring shape to minimize damage to the septum structure. The needle tips were beveled to a point with a 12° angle recommended for animal injections.

Septum samples were prepared for puncture experiments with 27 Ga and 30 Ga needles. To investigate the effect of the compression applied to the septum, one batch of samples (N=4) were fabricated without the septum cavity cap. Instead, the septa were fixed and sealed in the septum cavities using cyanoacrylate, thereby not compressing the septum. 30 Ga needles were used for this experiment and the results were compared with the samples with the septum cavity cap incorporating compression ring punctured with 27 Ga and 30 Ga needles (N=4 for each).

To test septum function, the space beneath the septum and 5 cm of the outlet tubing were filled with dyed DI water using the sharp (12°) non-coring needles and the septum samples were fixed in the pneumatic puncture device. The outlet tubing was placed on a ruler to enable quantification of fluid motion for leak testing. A signal generator provided a 0.2 Hz sinusoidal drive to the pneumatic actuator to repeatedly puncture the septum. The number of repetitive punctures was increased logarithmically using a step size of $10^{0.2}$, and leak testing was performed between each step. This leak testing involved gradual application of 100 kPa pneumatic back pressure at the outlet tubing for 1 minute.

Fluid displacement within the tubing was recorded with a digital microscope (USB-MICRO-250X, Plugable®, WA, USA) and analyzed with NIH-ImageJ, resulting in a resolution of 2.4 nL/min. Leakage was confirmed if a backward displacement of the fluid in the tubing was observed. If no leakage was observed, the test continued by switching on the signal generator until the next step. The number of punctures before leakage was found for each case based on the last value with no leakage.

Next, the reservoir cavity volume, backflow due to membrane restoring force, and total fluid extraction percentage for the three different reservoir cavity sizes were characterized. The reservoir cavity samples were fabricated and tested separately. Each sample comprised a reservoir membrane but with modifications to facilitate the test. The reservoir cavity inlet was directly connected to an inlet tubing, a three-way stopcock, and syringes for cavity filling, with an outlet tubing aligned over a ruler to quantify fluid movement due to pneumatic pressure applied to the region above the reservoir membrane.

A syringe was connected to the inlet port and pulled to remove air from the reservoir cavity and deform the reservoir membrane down to its minimum volume. The syringe was replaced with a three-way stopcock connected to the inlet tubing. Dyed DI water was injected to fill the inlet tube up to the entrance of the reservoir cavity via visual observation under a microscope. A small volume syringe was then connected via the stopcock to accurately quantify injected volume. With the outlet tubing open, the syringe was discharged until the fluid was observed to reach the drug storage device exit. The outlet tubing was then clamped closed and the syringe was discharged to fill the cavity, as confirmed by visual observation under a microscope. The three-way stopcock was then switched to block flow on the inlet side, the outlet tubing clamp was released, and the fluid volume in the outlet tubing was quantified. The reservoir cavity volume was calculated by subtraction of the fluid volume in the outlet tubing from the injected fluid volume from the syringe.

The backflow due to restoring force of the reservoir membrane was characterized for cavity fill volumes of approximately 80%, 60%, 40%, 20%, and 0%. Pneumatic pressure was applied above the reservoir membrane for 1 minute to induce forward fluid movement. After discharge of approximately 20% of the volume, the pneumatic pressure was released and the fluid front displacement in the outlet tubing was observed under a microscope for 4 minutes. Three different outlet tubing sizes were used for the three different reservoir cavity sizes to have a minimum resolution of 0.1% of the full capacity using a 0.5 mm graded ruler. The backflow of the fluid front was recorded and the experiment was repeated for the next 20% of the overall volume. The total fluid in the outlet tubing after the fifth step indicated the total extraction percentage. Three samples for each of the three different cavity sizes were tested with three replications (N=9 for each size, total N=27).

The integrated microsystem (drug storage device+micropump) was tested in vivo to evaluate its suitability for subcutaneous implantation, functionality for acute drug delivery to the mouse inner ear, and capability for long-term implantation. The drug delivery test was performed for the administration of sodium salicylate, leading to temporary hearing loss, i.e., reversible shifts of optoacoustic emissions thresholds and levels. Salicylate can act as a competitive antagonist at the anion-binding site of prestin, which causes reversible disruption of outer hair cell motility. Specifically, this disruption of prestin causes a reduction in distortion product optoacoustic emission (DPOAE) amplitudes and thresholds. Therefore, salicylate was delivered to the round window membrane (RWM) and auditory function was evaluated using DPOAE measurements. To evaluate long-term biocompatibility, the drug storage device was implanted for six months with frozen sections of surrounding tissue analyzed histologically for signs of inflammation.

Ketamine (120 mg/kg body weight) and xylazine (10 mg/kg body weight) were used in combination with topical application of 4% lidocaine for analgesia for the implant surgery. A young adult CBA/CaJ mouse was positioned on a servo-controlled heating pad maintaining aseptic conditions. When the proper plane of anesthetic was achieved (toe pinch, heart rate, respiratory rate), the upper back was then shaved and cleaned, and the microsystem was inserted subcutaneously in the center of the upper back via a small incision. Supplementary doses at one-third of the initial dose were administered as needed to maintain the proper levels of general anesthesia. Following insertion ventral to the dermis, medical grade adhesive (Loctite 4206, Rocky Hill, Conn.) was used to secure the wound closure, along with several stitches to close the incision over the microsystem.

Following data collection, the mouse was euthanatized (Euthasol®, 0.22 ml/kg, IP) and then perfused with 4% paraformaldehyde fixative transcardially. Next, tissue samples were dissected from around the microsystem and prepared for standard frozen sectioning followed by hematoxylin+eosin (H&E) tissue staining to visualize cellular locations and structure around the microsystem.

Two young adult (2-4 months of age) CBA/CaJ mice bred and raised in-house were used for this study. After subcutaneous implantation of the microsystems in the center of the upper back, a bullaostomy surgery was performed to prepare a site for infusion of the salicylate into the middle ear cavity. A mixture of ketamine (120 mg/kg body weight) and xylazine (10 mg/kg body weight) was injected via the intraperitoneal route to deeply anesthetize the mice for the bullaostomy surgery. The left ventral surface of the neck was then shaved and cleaned. Surgery was performed on the left (ipsilateral) ear. During infusions, each mouse was immobilized using anesthesia with supplementary doses at one-third of the initial dose administered as needed to maintain the proper levels of general anesthesia.

Auditory function was assessed via automated DPOAE threshold measurements at F2 frequencies of 8.9 kHz, 13.5 kHz, 17.9 kHz, 24.6 kHz, 35.8 kHz, and 51.4 kHz. Measurements performed before the surgery were used for a baseline to compare subsequent DPOAE threshold shifts.

The salicylate solution consisted of NaCl (120 mM), KCl (3.5 mM), $CaCl_2$) (1.5 mM), glucose (5.5 mM), HEPES buffer (4-(2-hydroxyethyl)-1-piperazineethanesulfonic acid, 20 mM), and sodium salicylate (50 mM). The pH was adjusted to 7.5 using NaOH. All solutions were prepared on the day of the experiment using sterile double-distilled water. The salicylate was loaded into a 25 µL sterilized syringe (1702 LT SYR, Hamilton Co., NV, USA) with a needle (33 Ga, 7747-01, point style 4, 12°, 1", Hamilton Co., NV, USA) and was de-bubbled. The drug storage device was filled by injection through refill port using the needle and the salicylate was pushed through the tubing using positive syringe pressure until it was 1 mm from the microtubing tip.

The infusion of the salicylate was enabled by a novel biocompatible, implantable, scalable, and wirelessly controlled peristaltic micropump. The micropump operation was controlled through Bluetooth communication using a custom-made Android application. The micropump in vitro characterization results showed that, by tuning the actuation frequency of the micropump, nanoliter resolution flow rate across the range of 10-100 nL/min is generated in the presence of 10× physiological inner ear backpressures and ±3° C. fluctuation in ambient temperature. It was also shown that the micropump could provide 50 nL/min for 20 minutes with 0.4% error in overall delivered drug volume, which was shown to temporarily impact the DPOAE threshold shift. The integrated micropump operation was optimized for working in the subcutaneous temperature of mice (~33° C.) in a fluid environment (glycerin) with similar thermal characteristics to subcutaneous tissues to provide a flow rate of 50 nL/min for long-term performance.

The overall footprints of the drug storage devices were 5.8 $mm^2 \times 3$ $mm^2$ (1 µL), 7.6 $mm^2 \times 4.6$ $mm^2$ (10 µL), and 14.5 $mm^2 \times 11.5$ $mm^2$ (100 µL) with a thickness of 3 mm for each device. In vitro experiments were performed to optimize the septum design and thickness for thousands of refilling injections without leakage and to quantify backflow due to restoring force after extraction of fluid. Further, the total volume of the reservoir cavities and total extraction percentage of them were assessed. The reservoir membrane experiments were performed on all three capacities to demonstrate the scalability of the design.

Figure 5A:
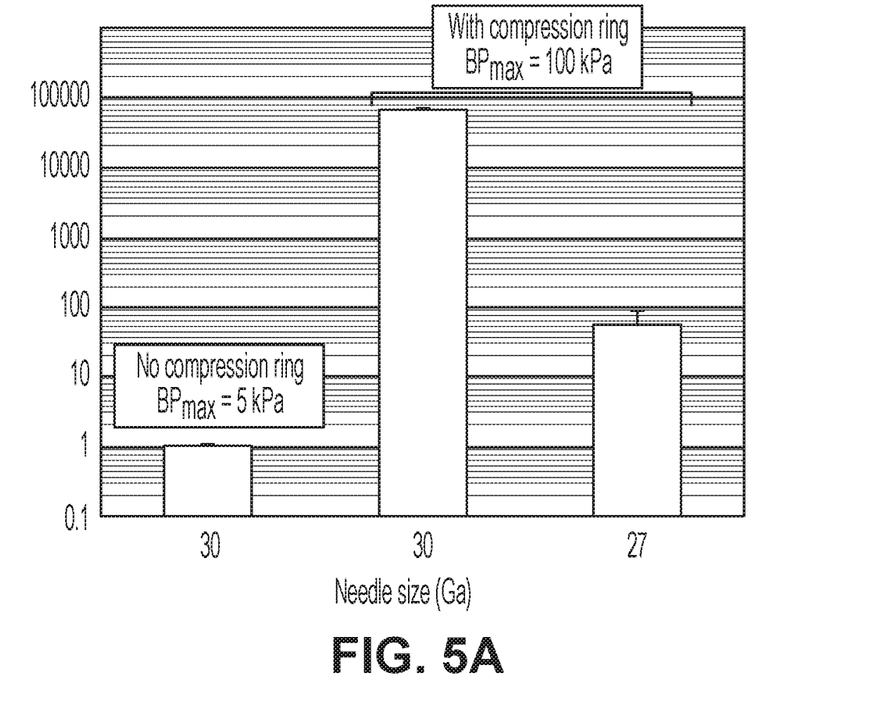
FIG. 5A is a graph that illustrates septum characterization results that show that non-compressed septa leak at less than 5 kPa backpressure with just one puncture with a 30 Ga needle, but compressing the septa increased the number of punctures before failure to approximately 65,000 at 100 kPa backpressure when puncturing with a 30 Ga needle.

The results shown in FIG. 5A indicate that the samples without the compression ring could not withstand a single puncture and leaked at backpressures as low as 5 kPa. In contrast, the samples with the compression ring withstood up to approximately 65,000 punctures without any leakage at 100 kPa backpressure using the 30 Ga needle. However, using the 27 Ga needle reduced the number of punctures without leakage to 55. Comparison between the results of the 30 Ga needle puncture with and without the compression ring indicates the significance of compression in increasing the septum lifetime. Further, the results of the 27 Ga punctures demonstrate the high endurance of this septum in taking up to 55 punctures, which is sufficient for many therapeutic development and clinical applications. Use of a 33 Ga needle (210 µm OD) dramatically enhances the robustness of the septum to levels that far exceed any practical use case. This smaller gauge needle was successfully used in the in vivo experiments with multiple successful subcutaneous injections in mice. All septum puncture experiments were performed on 1 mm thick septa. It is noted that the disclosed septum design can be employed in any refillable system.

Figure 5B:
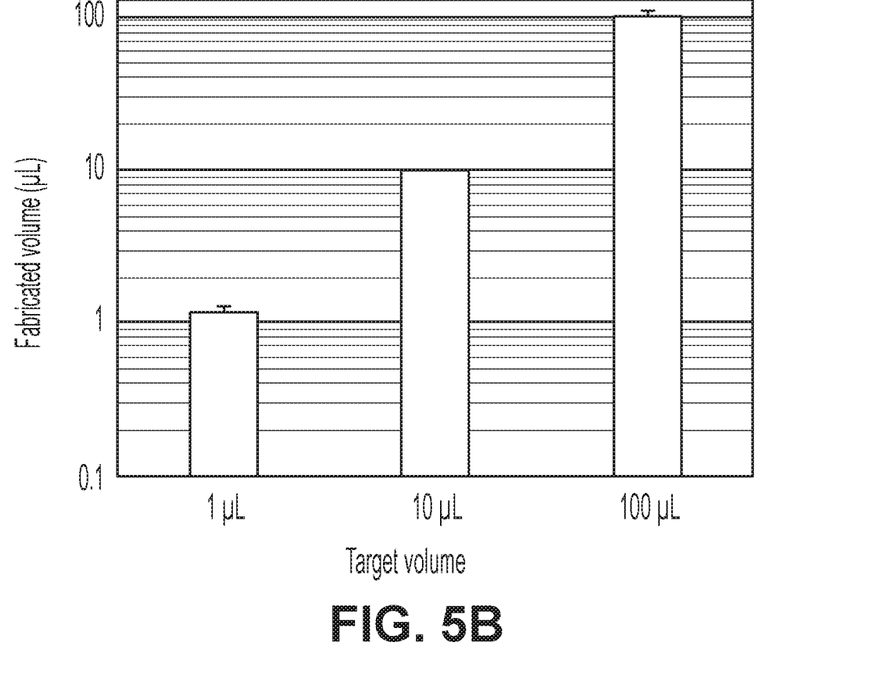
FIG. 5B is a graph that shows fabricated reservoir cavity volumes of 1.15±0.12 µL, 9.63±0.12 µL, and 100.04±9.43 µL for target volumes of 1 µL, 10 µL, and 100 µL.
Figure 5C:
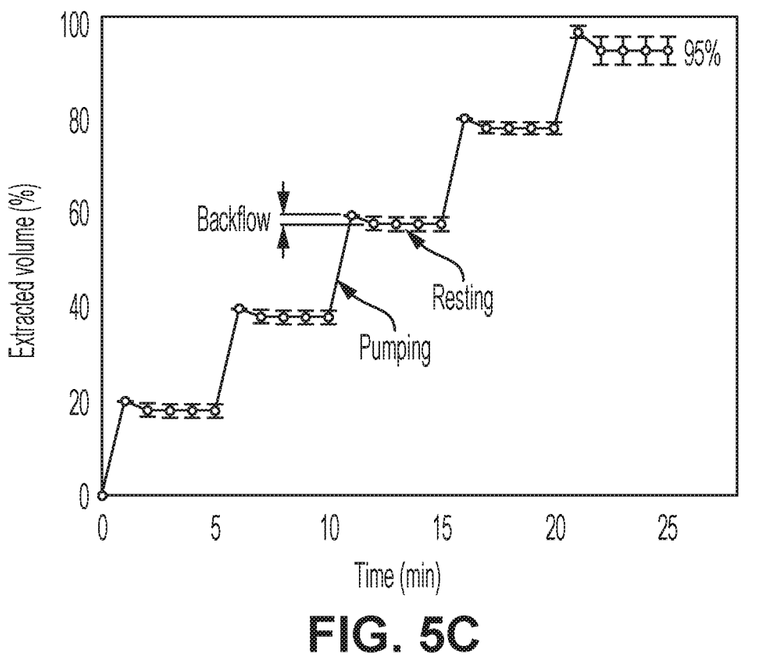
FIG. 5C is a graph that shows the average results for backflow due to restoring forces for 1 µL, 10 µL, and 100 µL reservoir cavity capacities normalized by the total volume of each cavity.
Figure 6:
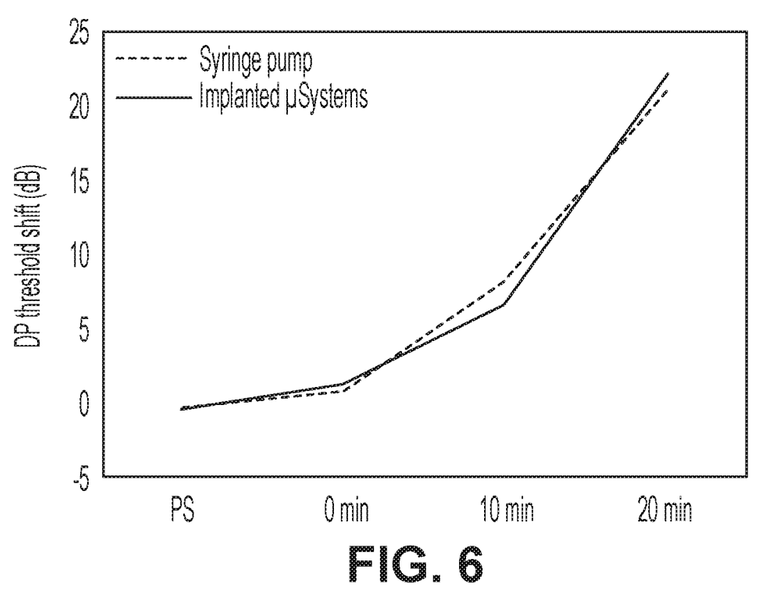
FIG. 6 is a graph that shows the results of the mean distortion product optoacoustic emission (DPOAE) threshold shift of the most basal cochlear region (F2=51.4 kHz) during salicylate delivery from an implanted microsystem.

The results indicate that the overall capacities of the cavities were 1.15±0.12, 9.63±0.12, and 100.04±9.43 (mean±SD) for target volumes of 1 µL, 10 µL, and 100 µL, as shown in FIG. 5B. FIG. 6 shows the average of extracted volume during pumping and resting for the three different capacities normalized by the total volume of each cavity. Each data point is an average of results from the three reservoir sizes, each with three samples and three replicates (N=27). The results show that, for all steps, the backflow was not significant compared to the overall size (2% average). The backflow at each step occurred relatively quickly after deactivation of pumping (<2 minutes for all cases), ensuring stable behavior of the reservoir membrane for long-term applications. Further, no significant difference in the backflow was observed across different extraction percentage, except for the last step, which defines the total extraction percentage of the cavities. The average total extraction percentage was 95%.

Reservoir membrane samples were also created having twice the thickness of the original membrane for each reservoir cavity size. Experiments (N=27) showed significantly more backflow due to restoring force (3.8% average). This significant difference ($p<0.001$) is directly related to the thickness of the membranes. As the membrane becomes thicker, their resistance to deformation increases, which results in higher restoring forces and greater backflow when the pneumatic pressure is released. It is hypothesized that the total extraction percentage is a function of the discrepancy between the surface area of the membrane and the substrate. If the membrane surface area is larger than the substrate when fully collapsed by the pneumatic pressure the membrane, wrinkles form on the substrate and it resists further pressure. When the pneumatic pressure is released, these areas induce restoring forces and backflow. On the other hand, if the membrane surface area is smaller than the substrate, there is space between the membrane and the substrate that cannot be swept by the membrane unless further pressure is applied, which restores when the pressure is released and causes backflow.

The integrated microsystem measured 19 $mm^3 \times 13$ $mm^3 \times 3$ $mm^3$ (L×W×H) enabling subcutaneous implantation in a mouse due to its planar form factor. To evaluate the functionality of the microsystem, the outlet microtubing of the microsystem was implanted at the RWM niche to deliver salicylate at 50 nL/min for 20 minutes, replicating a previous drug delivery system utilizing a syringe pump. Auditory function was measured during the infusion using the DPOAE method. Finally, the capability of the microsystem for long-term implantation was tested via standard frozen sectioning analysis of the tissue around it.

The accessibility of the refill port of the drug storage device was explored by palpation and observation of the raised peripheral ridge of the refill port when the shaved skin of the mouse was stretched. Subcutaneous injections through the mouse skin were successfully performed using a 33 Ga (210 µm OD) non-coring needle (7747-01, point style 4, 12°, 1", Hamilton Co., NV, USA), demonstrating in vivo validity of the larger 27 and 30 Ga syringe needles used for the septum characterization test.

Drug delivery experiments were performed using the integrated microsystem to show the performance of the system while implanted (two microsystems in two mice). Acute deliveries were performed to deliver salicylate at the RWM niche at 50 nL/min for 20 minutes, while the DPOAE threshold shifts were recorded during the infusion to replicate a previous experiment that was performed using a syringe pump. The Android application enabled read control of the device for staring/stopping the infusion. The results of the mean threshold shift of the most basal region ($F2=51.4$ kHz) for microsystems and the syringe pump are presented in FIG. 6. A baseline measurement was acquired approximately 10 to 15 minutes before the cannula placement surgery. The results compare the changes in DPOAE thresholds to baseline at four time-points: post-surgery (PS) in which DPOAE values were acquired immediately before the micropump was turned on, 0 minutes, the time at which the micropump was turned on, and 10 and 20 minutes after the onset of salicylate perfusion. There were mean shifts of 6.8 dB and 22.1 dB after 10 minutes and 20 minutes infusion for the implanted microsystems, suggesting the successful performance of the implanted microsystem.

The mouse recovered well from the surgery and, over the six-month survival period, was in good health. Post-implantation, the mouse was monitored daily and the results indicated that the overall health was excellent. This included no signs of fever or infection, no significant swelling, no redness or lumps around the micropump location or incision, no presence of discolored fluid, and no weight loss. Cage behaviors, including feeding, grooming, and drinking, were normal.

The histological processing of the tissue surrounding the microsystem revealed a significant fibrotic layer around it along with some ingrown hair follicles associated with the incision site. Otherwise, there were no cellular indications of infections or additional inflammatory responses, or abnormal cellular structures or responses.

The invention claimed is:

1. A fluid storage device comprising:
a rigid outer housing that defines a septum cavity, a reservoir cavity, and a channel that extends between the two cavities, the outer housing further defining an outlet in fluid communication with the reservoir cavity;
a septum provided within the septum cavity, the septum being made of an elastic polymer and facilitating refilling of the fluid storage device; and
a reservoir membrane that, with the rigid outer housing, defines a reservoir in the reservoir cavity, the reservoir membrane being deformed as fluid is drawn from the reservoir and including a thickness and material property combination that causes the reservoir membrane not to completely or partially return to its initial non-deformed shape even if the outlet of the device remains open after doses are administered.

2. The fluid storage device of claim 1, wherein the device has a height dimension no greater than 3 mm.

3. The fluid storage device of claim 1, wherein the outer housing comprises a base member, a septum cavity cap that covers the septum cavity, and a reservoir cavity cap that covers the reservoir cavity.

4. The fluid storage device of claim 3, wherein the septum cavity cap includes a refill port that provides access to the septum and the reservoir cavity cap includes one or more vent openings through which fluids can pass in and out of the reservoir cavity above the membrane.

5. The fluid storage device of claim 3, wherein each of the base member, the septum cavity cap, and the reservoir cavity cap are coated with a biocompatible polymer.

6. The fluid storage device of claim 3, wherein the septum cavity cap is configured to compress peripheral edges of the septum against an internal ledge of the base member to create radially inward compressive forces within the septum that enable the septum to close needle punctures to prevent leaking.

7. The fluid storage device of claim 6, wherein the septum cavity cap includes an annular compression ring on its bottom that compresses the septum.

8. The fluid storage device of claim 3, wherein the septum cavity cap includes a raised peripheral ridge on its top that facilitates location of the fluid storage device after the fluid storage device is implanted under the skin of a subject.

9. The fluid storage device of claim 3, further comprising a gasket that is positioned between the reservoir membrane and the reservoir cavity cap that seals the reservoir membrane within the reservoir cavity.

10. The fluid storage device of claim 1, wherein the septum is approximately 0.5 to 3 µm thick.

11. The fluid storage device of claim 1, wherein the septum is made out of biocompatible silicone and is coated with a biocompatible polymer.

12. The fluid storage device of claim 1, wherein the reservoir membrane has a thickness no greater than approximately 20 µm.

13. The fluid storage device of claim 1, wherein the reservoir membrane has an initial dome shape.

14. The fluid storage device of claim 1, wherein the reservoir membrane is made of parylene.

15. The fluid storage device of claim 1, wherein the reservoir membrane has a Young's modulus of approximately 1 MPa or 2 to 3 GPa.

16. The fluid storage device of claim 1, wherein the device is a normally open device that comprises no valves or other actuatable devices that are configured to impede the flow of fluid to and from the reservoir.

17. An implantable drug delivery system comprising: a fluid storage device including:
a rigid outer housing that defines a septum cavity, a reservoir cavity, and a channel that extends between the two cavities, the outer housing further defining an outlet in fluid communication with the reservoir cavity,
a septum provided within the septum cavity, the septum being made of an elastic polymer and facilitating refilling of the fluid storage device, and
a reservoir membrane that, with the rigid outer housing, defines a reservoir in the reservoir cavity, the reservoir membrane being deformed as fluid is drawn from the reservoir and including a thickness and material property combination that causes the reservoir membrane not to completely or partially return to its initial non-deformed shape even if the outlet of the device remains open after doses are administered; and
a micropump in fluid communication with the outlet of the fluid storage device configured to draw fluid from the device and administer it to a subject in which the drug delivery system is implanted.

18. The drug delivery system of claim 17, wherein the reservoir membrane has a thickness no greater than approximately 20 µm.

19. The drug delivery system of claim 17, wherein the reservoir membrane is made of parylene.

20. A membrane for use in a normally open drug delivery system, the membrane comprising:
an initially dome-shaped layer of a material having a thickness no greater than approximately 20 µm and a Young's modulus of approximately 2 to 3 GPa, that collapses in response to fluid being discharged from the normally open drug delivery system.

* * * * *